United States Patent
Kang (10) Patent No.: US 12,245,975 B2
(45) Date of Patent: Mar. 11, 2025

(54) MOTORIZED JOINT POSITIONER

(71) Applicant: MAKO Surgical Corp., Fort Lauderdale, FL (US)

(72) Inventor: Hyosig Kang, Weston, FL (US)

(73) Assignee: MAKO Surgical Corp., Fort Lauderdale, FL (US)

( * ) Notice: Subject to any disclaimer, the term of this patent is extended or adjusted under 35 U.S.C. 154(b) by 1107 days.

(21) Appl. No.: 16/787,492

(22) Filed: Feb. 11, 2020

(65) Prior Publication Data

US 2020/0170867 A1 Jun. 4, 2020

Related U.S. Application Data (63) Continuation of application No. 16/412,720, filed on May 15, 2019, now Pat. No. 12,036,155, which is a continuation of application No. 14/143,259, filed on Dec. 30, 2013, now Pat. No. 10,292,887.

(60) Provisional application No. 61/747,792, filed on Dec. 31, 2012.

(51) Int. Cl.
| | |
|---|---|
| *A61G 13/00* | (2006.01) |
| *A61B 5/00* | (2006.01) |
| *A61B 34/10* | (2016.01) |
| *A61B 34/20* | (2016.01) |
| *A61B 34/30* | (2016.01) |

(Continued)

(52) U.S. Cl.
CPC ........ *A61G 13/0063* (2016.11); *A61B 5/4528* (2013.01); *A61B 34/10* (2016.02); *A61B 34/20* (2016.02); *A61B 34/30* (2016.02); *A61G 13/1245* (2013.01); *A61G 13/125* (2013.01); *A61B 2090/061* (2016.02); *Y10S 901/02* (2013.01)

(58) Field of Classification Search
CPC ......... A61B 34/30; A61B 34/70; A61B 34/71; A61B 34/75; A61B 34/77; A61B 34/10; A61B 6/04; A61B 6/0407; A61B 6/0421; A61G 13/0063; A61G 13/0081; A61G 13/0036; A61G 13/1235; A61G 13/1245; A61G 13/125; A61G 13/1285; A61G 7/07; A61G 7/072; A61G 7/075; A61G 7/0755; A61H 1/02; A61H 1/0203; A61H 1/0218; A61H 1/0237; A61H 1/024; A61H 1/0244; A61F 5/04; A61F 5/042; A61F 5/048; A61F 5/37
USPC ........................................................ 128/882
See application file for complete search history.

(56) References Cited

U.S. PATENT DOCUMENTS

| | | |
|---|---|---|
| 3,753,557 A | 8/1973 | Kelley |
| 4,367,869 A | 1/1983 | Dailey et al. |
| 4,407,277 A | 10/1983 | Ellison |

(Continued)

OTHER PUBLICATIONS

U.S. Appl. No. 07/677,087, filed Mar. 29, 1991, Allen.
U.S. Appl. No. 13/719,008, filed Dec. 18, 2012, Mako Surgical Corp.

*Primary Examiner* — Adam Baker
(74) *Attorney, Agent, or Firm* — FOLEY & LARDNER LLP (57) ABSTRACT

A robot-aided knee arthroplasty system includes a robotic device and a controller communicable with the robotic device. The controller is configured to control the robotic device to apply a force configured to increase a gap distance between a femur and a tibia of a knee joint and collect measurements of the gap distance between the femur and the tibia as the robotic device applies the force.

15 Claims, 5 Drawing Sheets

(51) Int. Cl.
*A61G 13/12* (2006.01)
*A61B 90/00* (2016.01)

(56) References Cited

U.S. PATENT DOCUMENTS

| | | | |
|---|---|---|---|
| 4,705,026 A | 11/1987 | Chaussy et al. | |
| 4,834,073 A | 5/1989 | Bledsoe et al. | |
| 4,909,262 A | 3/1990 | Halpern et al. | |
| 4,974,830 A | 12/1990 | Genovese et al. | |
| 5,007,912 A | 4/1991 | Albrektsson et al. | |
| 5,025,802 A | 6/1991 | Laico et al. | |
| 5,063,918 A | 11/1991 | Guhl | |
| 5,290,220 A | 3/1994 | Guhl | |
| 5,397,329 A | 3/1995 | Allen | |
| 5,575,794 A | 11/1996 | Walus et al. | |
| 5,645,079 A | 7/1997 | Zahiri et al. | |
| 5,984,930 A | 11/1999 | Maciunas et al. | |
| 6,033,415 A | 3/2000 | Mittelstadt et al. | |
| 6,187,018 B1 | 2/2001 | Sanjay-Gopal et al. | |
| 6,234,173 B1 | 5/2001 | Hajianpour | |
| 7,302,288 B1 | 11/2007 | Schellenberg | |
| 7,381,192 B2* | 6/2008 | Brodard | A61H 1/0255 601/5 |
| 7,934,687 B2 | 5/2011 | Crook et al. | |
| 8,010,180 B2 | 8/2011 | Quaid et al. | |
| 8,303,575 B2 | 11/2012 | Rodriguez Y Baena | |
| 8,460,277 B2 | 6/2013 | Suarez et al. | |
| 8,753,346 B2 | 6/2014 | Suarez et al. | |
| 9,615,987 B2 | 4/2017 | Worm et al. | |
| 2002/0193683 A1 | 12/2002 | Danielsson et al. | |
| 2004/0003468 A1* | 1/2004 | Mitsuishi | A61H 1/0255 5/624 |
| 2004/0106861 A1 | 6/2004 | Leitner | |
| 2005/0070834 A1 | 3/2005 | Herr et al. | |
| 2005/0160533 A1 | 7/2005 | Boucher et al. | |
| 2005/0234327 A1 | 10/2005 | Saracen et al. | |
| 2006/0130594 A1 | 6/2006 | Ikeuchi | |
| 2006/0142657 A1* | 6/2006 | Quaid | A61B 90/37 600/424 |
| 2007/0038161 A1 | 2/2007 | Bonutti et al. | |
| 2007/0142823 A1 | 6/2007 | Prisco et al. | |
| 2007/0270685 A1 | 11/2007 | Kang et al. | |
| 2008/0132818 A1 | 6/2008 | Livorsi | |
| 2008/0132897 A1 | 6/2008 | Livorsi et al. | |
| 2008/0281343 A1 | 11/2008 | Dewey et al. | |
| 2009/0005677 A1 | 1/2009 | Weber et al. | |
| 2009/0012531 A1 | 1/2009 | Quaid et al. | |
| 2009/0018445 A1 | 1/2009 | Schers et al. | |
| 2009/0088634 A1 | 4/2009 | Zhao et al. | |
| 2009/0198126 A1 | 8/2009 | Klingenbeck-Regn | |
| 2010/0160987 A1 | 6/2010 | Simmons | |
| 2010/0192961 A1 | 8/2010 | Amiot et al. | |
| 2010/0313897 A1 | 12/2010 | Schaeffer | |
| 2010/0332031 A1 | 12/2010 | Itkowitz et al. | |
| 2011/0004224 A1 | 1/2011 | Daigneault et al. | |
| 2011/0082468 A1 | 4/2011 | Hagag et al. | |
| 2011/0130688 A1 | 6/2011 | Nakamura et al. | |
| 2011/0238080 A1 | 9/2011 | Ranjit et al. | |
| 2012/0046540 A1* | 2/2012 | Branch | A61B 5/459 600/407 |
| 2012/0186020 A1 | 7/2012 | Malakhov | |
| 2012/0265071 A1 | 10/2012 | Berke | |
| 2012/0318278 A1 | 12/2012 | Aboujaoude et al. | |
| 2013/0072821 A1 | 3/2013 | Odermatt et al. | |
| 2013/0096573 A1 | 4/2013 | Kang et al. | |
| 2013/0096574 A1 | 4/2013 | Kang et al. | |
| 2013/0110129 A1 | 5/2013 | Reid et al. | |
| 2013/0125311 A1 | 5/2013 | Marugg | |
| 2013/0172905 A1 | 7/2013 | Iorgulescu et al. | |
| 2013/0204119 A1 | 8/2013 | Coelho Do Sameiro Espregue Mendes | |
| 2013/0211420 A1 | 8/2013 | Jensen | |
| 2013/0218137 A1 | 8/2013 | Abovitz et al. | |
| 2013/0346348 A1 | 12/2013 | Buehler et al. | |
| 2014/0163377 A1 | 6/2014 | Kang et al. | |
| 2014/0171962 A1 | 6/2014 | Kang | |
| 2014/0180290 A1 | 6/2014 | Otto et al. | |
| 2014/0180341 A1 | 6/2014 | Kang et al. | |
| 2014/0188132 A1 | 7/2014 | Kang | |

* cited by examiner

MOTORIZED JOINT POSITIONER

CROSS-REFERENCE TO RELATED APPLICATION

This application is a continuation of U.S. application Ser. No. 16/412,720, filed May 15, 2019, which is a continuation of U.S. application Ser. No. 14/143,259, filed Dec. 30, 2013, which claims the benefit of and priority to U.S. Provisional Application No. 61/747,792, filed Dec. 31, 2012. Each of the aforementioned applications is incorporated by reference herein in its entirety.

BACKGROUND

The present disclosure relates generally to the field of devices used to position a joint in connection with a medical procedures. Devices that hold a portion of a patient's anatomy (e.g., arm holders, leg holders, etc.) are useful in the medical industry to position and stabilize a patient's joint.

Some drawbacks of conventional joint positioners include the time and effort required to adjust the position of the patient's joint. For example, some joint positioners require a user to perform a mechanical adjustment to adjust the joint position. Adjusting such a positioner increases the time required to complete the medical procedure, and users may find it cumbersome or difficult to achieve a precise adjustment.

SUMMARY

The present application is directed to a motorized joint positioner that allows a user to quickly and accurately position a patient's joint. A user may wish to position a patient's joint, for example, in a doctor's office or during a surgical procedure. The user can easily and effectively maintain or adjust the position of the patient's joint using the motorized joint positioner described herein, which may increase efficiency in the doctor's office or operating room. In one embodiment, the positioner may be used to assist a surgeon during soft tissue balancing. In other embodiments, the motorized joint positioner includes features that are advantageous when the motorized joint positioner is being used in connection with a computer-assisted surgery ("CAS") system. These features include a local tracking system to track a portion of the patient's anatomy and a two-dimensional ultrasound array to enable registration of a portion of the patient's anatomy.

According to one exemplary embodiment, a motorized joint positioner includes a first robotic arm coupled to a first holder and a second robotic arm coupled to a second holder. At least one of the first and second robotic arms includes an actuator controllable to position the corresponding first or second holder.

According to another exemplary embodiment, a motorized joint positioner system includes a motorized joint positioner having first and second robotic arms, wherein at least one of the first and second robotic arms includes a series elastic actuator. The system further includes a processing circuit configured to position the motorized joint positioner by controlling the series elastic actuator. The motorized joint positioner is backdrivable such that it can be manually repositioned by a user.

Alternative exemplary embodiments relate to other features and combinations of features as may be generally recited in the claims.

BRIEF DESCRIPTION OF THE FIGURES

The disclosure will become more fully understood from the following detailed description, taken in conjunction with the accompanying figures, wherein like reference numerals refer to like elements, in which.

DETAILED DESCRIPTION

Exemplary Motorized Joint Positioner

Before turning to the figures, which illustrate the exemplary embodiments in detail, it should be understood that the application is not limited to the details or methodology set forth in the description or illustrated in the figures. It should also be understood that the terminology is for the purpose of description only and should not be regarded as limiting.

The motorized joint positioner described herein can be used in any context to position a joint. For example, surgeons may use the motorized joint positioner prior to or during a surgical procedure. Other medical professionals may use the motorized joint positioner during examination, testing, or imaging of the joint. The motorized joint positioner can also be used to position a variety of different joints, such as a knee, hip, ankle, elbow, shoulder or wrist.

Figure 1:
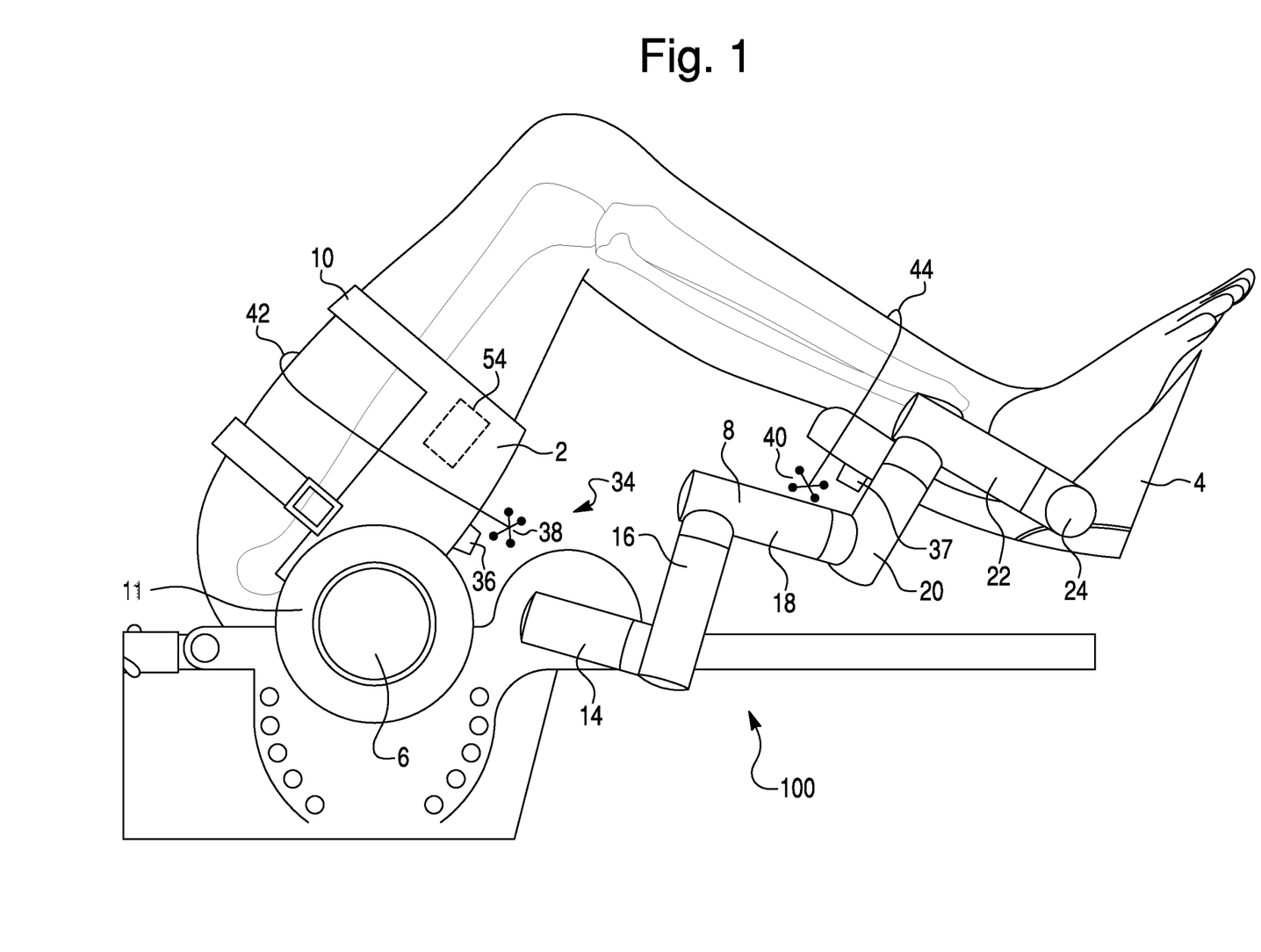
FIG. 1 is a side view of a motorized joint positioner, according to an exemplary embodiment.
Figure 2:
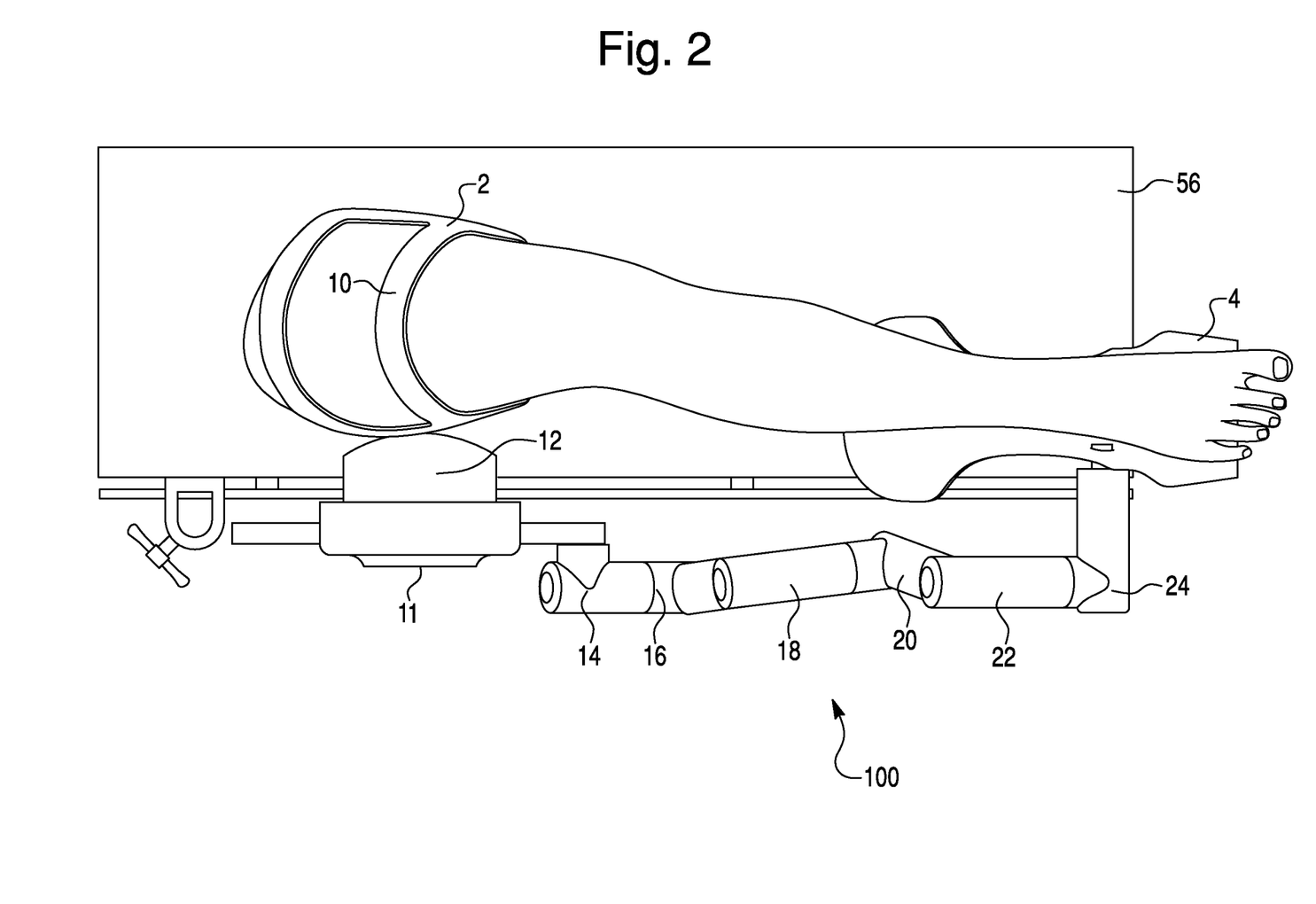
FIG. 2 is a top view of the motorized joint positioner of FIG. 1.

Referring to FIGS. 1 and 2, a motorized joint positioner 100 according to an exemplary embodiment includes a first holder 2 and a second holder 4. The first holder 2 is coupled to a first robotic arm 6 and the second holder 4 is coupled to a second robotic arm 8. The robotic arms 6, 8 are driven by actuators, such as series elastic actuators (SEAs). In the figures, the motorized joint positioner 100 is illustrated during positioning of a knee.

The first and second holders 2, 4 can be any suitable structure for holding a portion of a patient. In the embodiment shown in FIG. 1, the holders 2, 4 are cuffs. The patient's upper leg (e.g., thigh) rests in holder 2, and the patient's lower leg (e.g., ankle) rests in holder 4. The holders 2, 4 may further include one or more straps 10 for securing the patient to the holders 2, 4.

Positioning

The robotic arms 6, 8 can each include one or more SEAs. The SEAs may be any commercially available SEA and may be rotational or linear actuators. The SEAs are configured to enable force-control and high-precision position control of the robotic arms. Multiple SEAs can be linked, as shown in FIG. 1, to provide position control in numerous degrees of freedom. In one embodiment, the first robotic arm 6 is a two degree-of-freedom (DOF) robotic arm that includes a first joint 11 and a second joint 12 (FIG. 2), and the second robotic arm 8 is a six DOF robotic arm that includes a first joint 14, a second joint 16, a third joint 18, a fourth joint 20, a fifth joint 22, and a sixth joint 24 (FIG. 1). Each joint can be controlled by a corresponding SEA. However, as many joints (and corresponding SEAs to control the joints) as desired may be linked to form robotic arms with the desired degrees of freedom. Rotational or linear SEAs may be chosen to obtain a compact design of the first and second robotic arms 6, 8.

Figure 4:
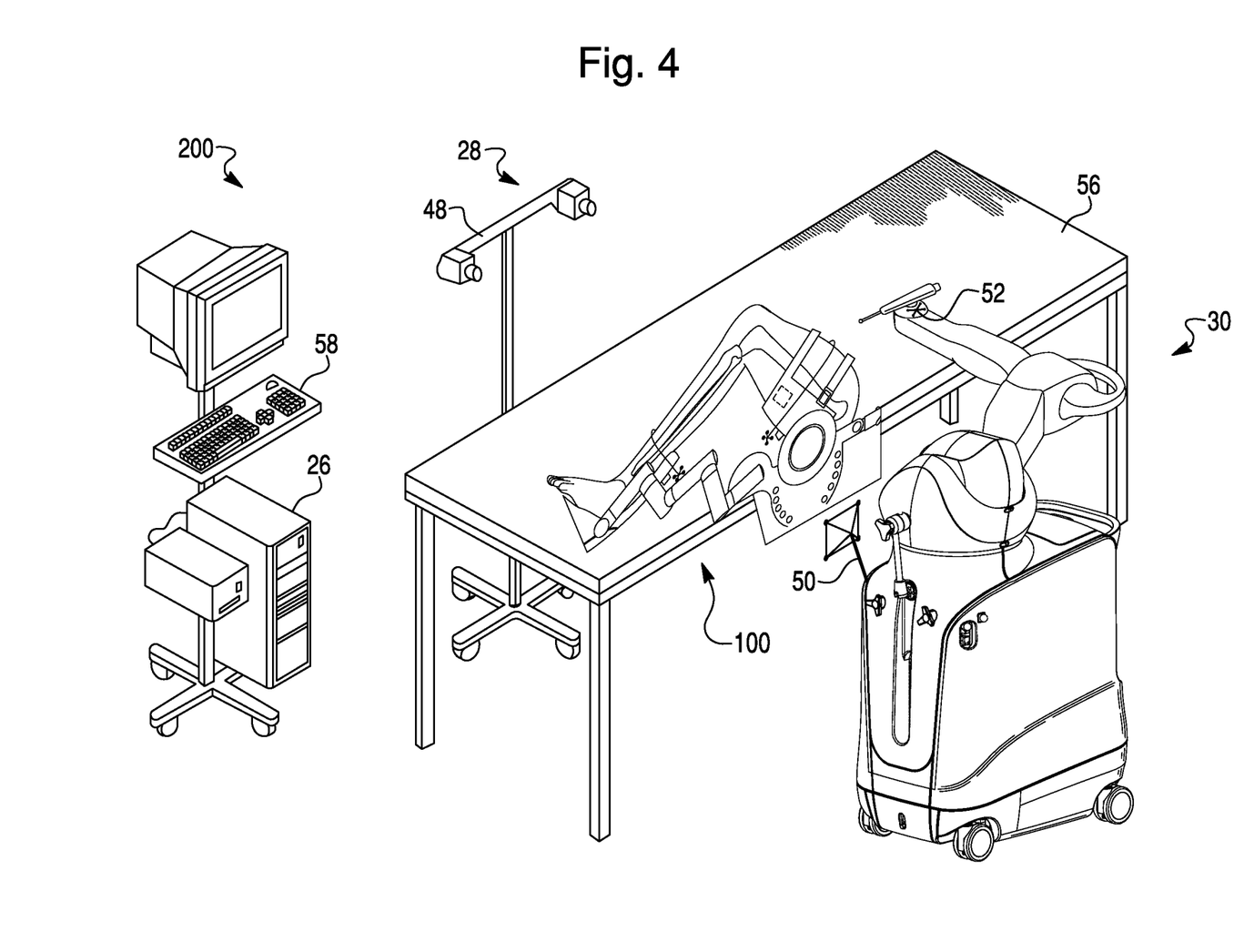
FIG. 4 is an exemplary embodiment of a computer-assisted surgery system that includes a motorized joint positioner.

Referring to FIG. 4, the joint positioner 100 may be used in connection with a CAS system 200. The CAS system 200 may include, among other things, the motorized joint positioner 100, a processing circuit (represented in the figures as a computer 26), a secondary tracking system 28, and a haptic device 30. The haptic device 30 is an interactive robotic device used by a surgeon during a surgical procedure, such as the robotic device described in U.S. Pat. No. 8,010,180, titled "Haptic Guidance System and Method," which is hereby incorporated by reference herein in its entirety.

Figure 3:
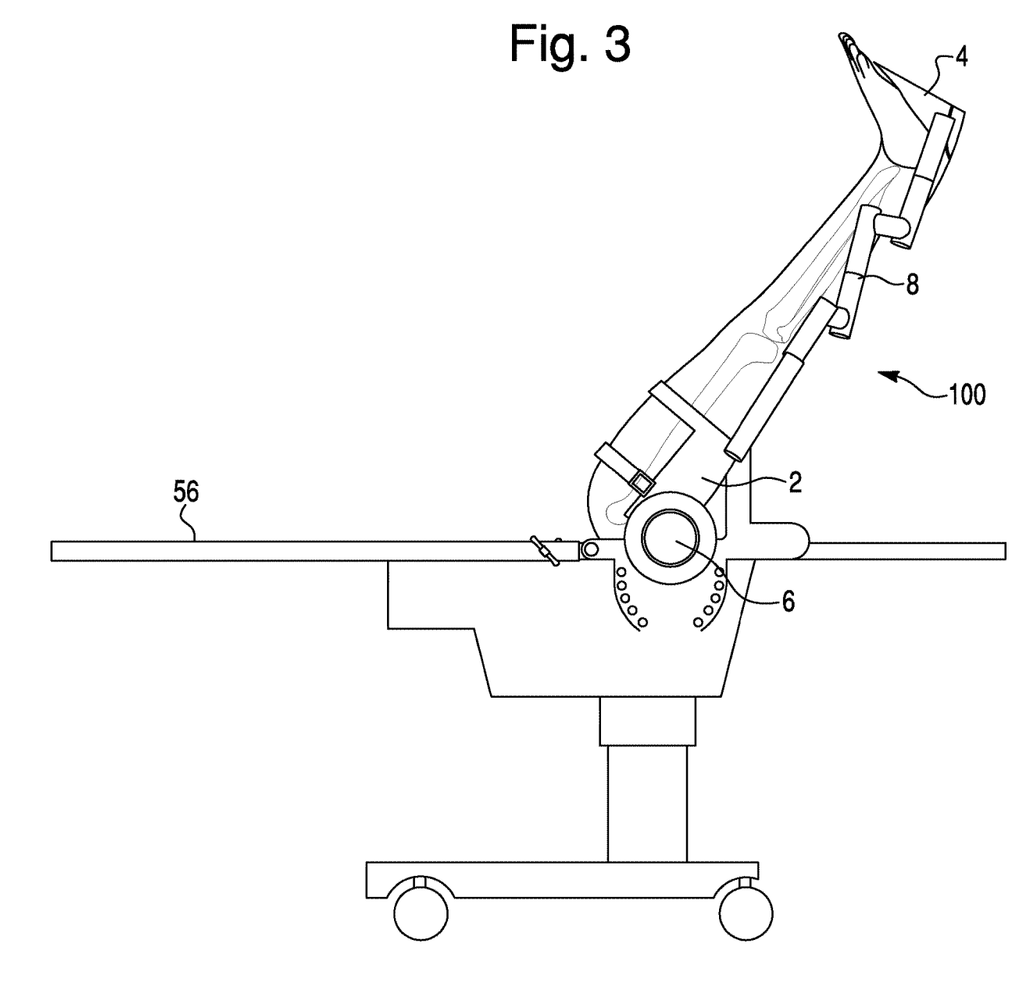
FIG. 3 is a motorized joint positioner holding a patient's knee in an extended position, according to an exemplary embodiment.

The joint positioner 100 can be controlled (e.g., by computer 26 or manually by a user) to position the patient's joint. For example, the patient's knee may be brought from the flexed position shown in FIGS. 1 and 2 to the fully extended position shown in FIG. 3. The computer 26 may control the motorized joint positioner 100 to bring the holders 2, 4 (and thus the portion of the patient held by the holders 2, 4) to a desired position based on a preoperative surgical plan. During a surgical procedure, the computer 26 can control the motorized joint positioner 100 to bring the holders 2, 4 to positions corresponding to different stages of a surgical plan. For example, if a certain stage of a knee replacement surgery requires the femur and tibia to be pulled away from each other, the computer 26 can be programmed to control the motorized joint positioner 100 to accomplish this positioning.

The force control capabilities of the SEAs enable the motorized joint positioner 100 to fully compensate for the weight of the patient's extremity or other body part held by the positioner 100. In one embodiment, the motorized joint positioner 100 applies forces to the first and second holders 2, 4 to counteract the weight of a portion of a patient's anatomy held by the motorized joint positioner (e.g., the patient's leg). This gravity compensation feature causes the portion of the patient to feel weightless as a user is manually repositioning the joint positioner 100. Consequently, the user is able to manually reposition the joint positioner 100 without having to exert additional effort to lift or move the weight of the portion of the patient's anatomy. The backdrivability of the SEAs further contribute to the ease with which a user can manually adjust the motorized leg positioner 100 (i.e., manually adjust the position of the first and second holders 2, 4).

In one embodiment, the motorized joint positioner 100 has two modes. In the first mode, the positioner 100 may be utilized to hold the joint in a fixed position. This first mode is useful, for example, while a surgeon is using haptic device 30 to sculpt or otherwise modify the patient's joint. In one embodiment, the CAS system 200 is programmed to hold the positioner 100 in a fixed position while the haptic device 30 is in a cutting mode (i.e., when the surgical tool coupled to the haptic device is being operated). The surgeon can set the desired position of the joint positioner 100 by manually positioning the joint positioner 100 and then alerting the CAS system 200 to fix the position of the joint positioner 100. For example, once the joint positioner 100 is in a desired position, the surgeon can use input device 58 to set the joint positioner 100 in the first mode, thus fixing the joint positioner 100. The motorized joint positioner 100 may have a second mode in which a user can manually adjust the position of the motorized joint positioner 100. This second mode is useful during steps of a medical procedure in which it is advantageous for a surgeon to reposition the patient's joint, such as during surgical planning. The SEA actuators within the robotic arms 6, 8 provide a backdrivable system, allowing the user to manually manipulate the positions of the first and second holders 2, 4. The CAS system 200 determines how much force is required to compensate for the weight of the patient's leg and can sense incremental changes in force as a user manipulates the position of the joint positioner 100.

The processing circuit of the CAS system 200 is utilized to implement the various functions (e.g., calculations, control mechanisms, processes) described herein, such as computerized control of the motorized joint positioner 100. The processing circuit includes a processor and memory. The processor can be implemented as a general purpose processor, an application specific integrated circuit (ASIC), one or more field programmable gate arrays (FPGAs), a group of processing components, or other suitable electronic processing components. The memory (e.g., memory, memory unit, storage device, etc.) is one or more devices (e.g., RAM, ROM, Flash memory, hard disk storage, etc.) for storing data and/or computer code for completing or facilitating the various processes and functions described in the present application. The memory may be or include volatile memory or non-volatile memory. The memory may include database components, object code components, script components, or any other type of information structure for supporting the various activities and information structures described in the present application. According to an exemplary embodiment, the memory device is communicably connected to the processor and includes computer code for executing one or more processes described herein.

The joint positioner 100 may communicate with the computer 26 via a communication interface. The communication interface can be or include wired or wireless interfaces (e.g., jacks, antennas, transmitters, receivers, transceivers, wire terminals, etc.) for conducting data communications with external sources via a direct connection or a network connection (e.g., an Internet connection, a LAN, WAN, or WLAN connection, etc.). For example, the communication interface can include an Ethernet card and port for sending and receiving data via an Ethernet-based communications link or network. In another example, the communication interface can include a WiFi transceiver for communication via a wireless communications network.

Soft Tissue Balancing

Figure 5A:
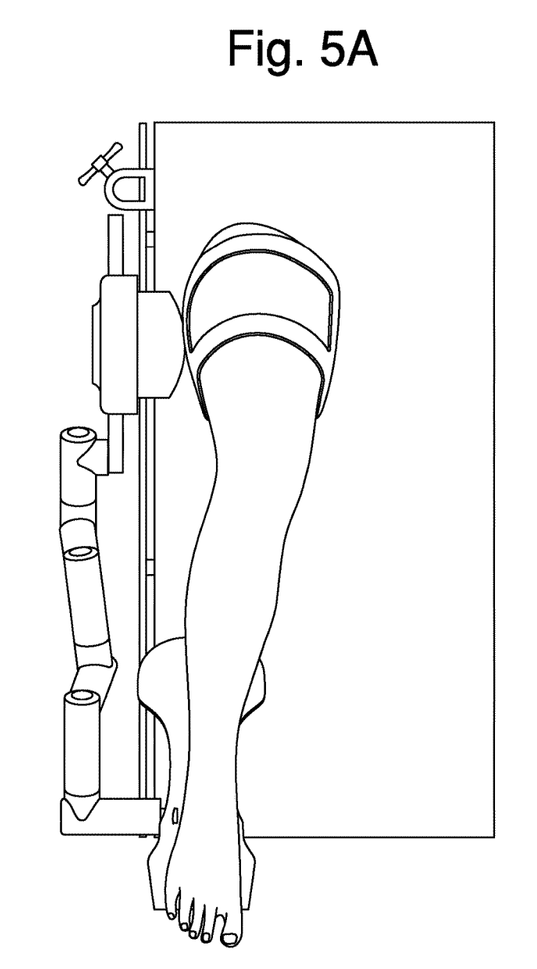
FIGS. 5A and 5B illustrate a motorized joint positioner being utilized for soft tissue balancing, according to an exemplary embodiment.
Figure 5B:
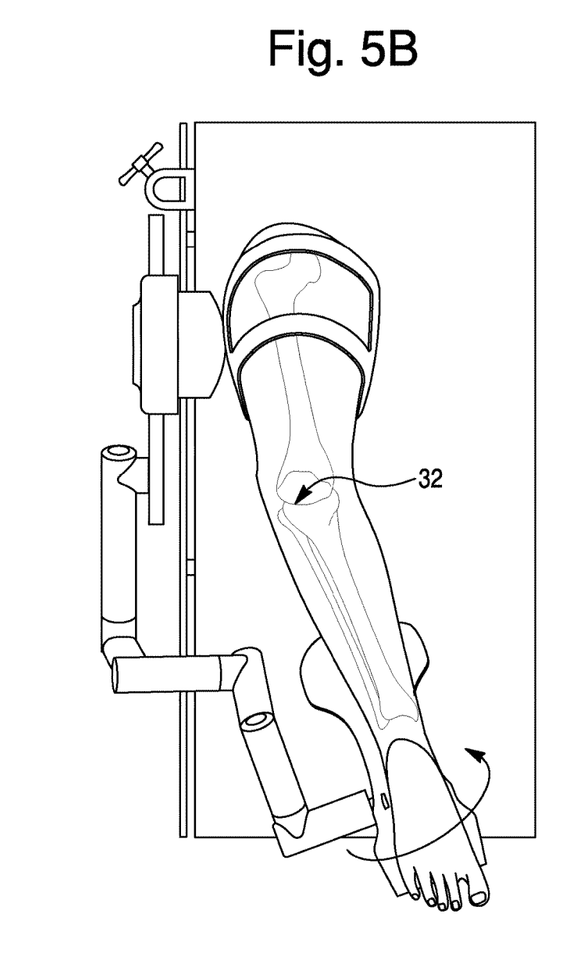

Referring to FIG. 5, the motorized joint positioner 100 may enable computerized soft tissue balancing during joint repair surgeries. For example, an important part of some knee replacement surgeries is achieving an acceptable balance of the ligaments surrounding the knee. Conventionally, to achieve the desired soft tissue balance during a surgical procedure, a surgeon manually manipulates the patient's knee to determine the tension of soft tissue during various movements. The joint positioner 100 described herein can assist the surgeon during balancing by moving the patient's joint through a range of motion and providing measurements representative of the tension in the patient's joint. An example of a measurement representative of the tension in a patient's joint is the distance of gap 32 between two bones of the joint (e.g., between the patient's femur and tibia). The joint positioner 100 is able to provide known forces or torques to the patient's joint to obtain measurements related to the joint's tension.

In one embodiment, the joint positioner 100 moves the patient's joint prior to surgery to obtain a preoperative set of data representative of the patient's soft tissue balance. The preoperative set of data may include, for example, the distance of gap 32 in the patient's knee when the joint is in a neutral position (FIG. 5A) and when a known amount of torque is applied to the patient's knee (FIG. 5B). Preoperative data may further include forces acting on the joint, such as forces resisting movement, while the patient's joint is being positioned or guided through a range of motion. The joint positioner 100 can then be used during a surgical procedure to move the patient's joint with a trial implant in place, deriving another set of data. The surgeon can compare the data obtained with the trial implant to the preoperative data and use the information, for example, to choose an alternative shape or size of implant or to make other modifications to the knee. Once the surgeon believes the surgical operation is complete, the joint positioner 100 can be used to obtain a final set of data representative of the patient's postoperative soft tissue balance. In this manner, the joint positioner 100 helps surgeons obtain a desired soft tissue balance, which may be similar to or different from the balance of the patient's preoperative joint.

Local Tracking System

In one embodiment, the joint positioner 100 includes a local tracking system 34 to track a portion of a patient's anatomy (e.g., the portion held by the joint positioner 100) relative to the joint positioner 100. The tracking system 34 can be optical or mechanical. In FIG. 1, the tracking system 34 is an optical tracking system that includes at least one detection device 36 and trackable markers 38, 40. The tracking system 34 may further include a second detection device 37. The detection devices 36, 37 are fixed to the first and second holders 2, 4, respectively. The trackable markers 38, 40 are fixed to the portion of the patient's anatomy (e.g., the patient's bones) held by the joint positioner 100 and are detectable by the detection devices 36, 37. In one embodiment, the detection devices 36, 37 include a visible light-based detector, such as a MicronTracker (Claron Technology Inc., Toronto, Canada), that detects a pattern (e.g., a checkerboard pattern) on the trackable markers 38, 40. As is known, the trackable markers 38, 40 may be active (e.g., light emitting diodes or LEDs) or passive (e.g., reflective spheres, a checkerboard pattern, etc.) and have a unique geometry (e.g., a unique geometric arrangement of the markers) or, in the case of active, wired markers, a unique firing pattern. The trackable markers 38, 40 are affixed to the tracked objects (e.g., the patient's bones), in a secure and stable manner. In one embodiment, the trackable markers 38, 40 are fixed to the patient's bones with bone pins 42, 44. In operation, the detection device 36 detects positions of the trackable markers 38, 40, and the pose of the tracked object (e.g., the patient's bones) relative to the detection device(s) 36, 37 can be calculated based on the trackable elements' positions, unique geometry, and known geometric relationship to the tracked objects. In this manner, the pose of the tracked objects (e.g., the patient's bones) can be calculated relative to the joint positioner 100.

In another embodiment, the detection device 24 is a three-dimensional tracking sensor, such as the 3D tracking sensor developed by Leap Motion, Inc. (San Francisco, CA). The three-dimensional tracking sensor is able to track the pose of the trackable markers 26, 28, as described in U.S. application Ser. No. 13/714,066, titled "Registration and Navigation Using a Three-Dimensional Tracking Sensor," filed Dec. 13, 2012, which is hereby incorporated by reference herein in its entirety.

Inclusion of a local tracking system 34, as shown in FIG. 1, may provide advantages over use of a non-local (i.e., global) tracking system to track the portion of the patient's anatomy. Some types of global tracking systems utilize a detection device fixed relative to an operating room. The operating room may contain various tracked objects, such as the patient's bones and surgical tools. If the global tracking system is an optical tracking system, a line of sight from the trackable elements and the detection device may be required. If objects or people block the path from the trackable elements to the detection device, an interference in the tracking process may result. Use of a local tracking system 34, as shown in FIG. 1, minimizes line of sight issues by placing the detection device(s) 36 in close proximity to the trackable elements 26, 28. In this manner, the local tracking system 34 can continuously track the position of the patient's bones, which are coupled to the trackable elements 38, 40 via bone pins 42, 44.

In one embodiment, shown in FIG. 4, the CAS system 200 includes both a local tracking system 34 and a secondary, global tracking system 28. The secondary tracking system 28 can be used to track additional objects in the CAS system 200, and may include a secondary detection device 48 and additional trackable markers 50, 52. In one embodiment, trackable marker 50 is located on the base of haptic device 30, and trackable marker 52 is located on or near a surgical tool for use during a surgical procedure.

The local tracking system 34 may be in communication with the global tracking system 28 such that the position of all tracked objects in CAS system 200 can be calculated with respect to a single coordinate frame of reference. In one embodiment, an additional trackable marker is placed on a stationary portion of the joint positioner 100. This additional trackable marker is tracked by the secondary tracking system 28. The CAS system 200 can use the pose of the additional trackable marker to correlate the coordinate systems of the local tracking system 34 and the secondary tracking system 28. In another embodiment, a mechanical tracking system is coupled to the motorized leg positioner 100 (e.g., to the detection device 36 or to another portion of the motorized leg positioner 100). The mechanical tracking system is used to track the motorized leg positioner 100. The CAS system 200 can use information from the mechanical tracking system to correlate the coordinate systems of the local tracking system 34 and the secondary tracking system 28.

Registration

In one embodiment, the joint positioner 100 includes features useful for registration of the patient's anatomy (e.g., the bones held by joint positioner 100) to a three-dimensional representation of the portion of the patient's anatomy. The portion of the patient's anatomy is registered to allow the local tracking system 34 (or the global tracking system 28) to accurately monitor the position of the portion of the patient's anatomy during a medical procedure. In one embodiment, the joint positioner 100 includes an XY array of ultrasound transducers 54, as described in U.S. patent Ser. No. 13/710,955, titled "Registration Using Phased Array Ultrasound," filed Dec. 11, 2012, which is hereby incorporated by reference herein in its entirety. The array 54 may be located on the interior of one or both holders 2, 4, such that the array 54 is able to scan the patient's bone structure or soft tissue. The array is communicably coupled to the processing circuit (i.e., computer 26) for controlling the ultrasound transducers and for registering the portion of the patient's anatomy to a three-dimensional representation of the portion of the patient's anatomy. The three-dimensional representation may be obtained by any known imaging techniques (e.g., CT or MM). Alternatively, the three-dimensional representation may be obtained using an imageless system. Imageless systems include technologies that are known in the art, such as systems utilizing statistically shaped models and methods of bone morphing.

In one method of registration using the motorized joint positioner 100, the location of the joint positioner 100 is known. The location of the joint positioner 100 is known either by fixing a portion of the joint positioner 100 (e.g., to a table 56) or by tracking the joint positioner 100 with a tracking system such as secondary tracking system 28. If the array 54 is fixed to the joint positioner 100, the location of the array 54 can also be determined. The array 54 is controlled to create an acoustic wave directed towards a portion of the patient's anatomy suitable for registration (e.g., a portion of bone or soft tissue having features that can be aligned with the three-dimensional representation of the bone). Because the location of the array 54 is known, the location of bone scanned by the array 54 can be calculated. This information can be used to register the portion of the patient's anatomy to the three-dimensional representation.

Including an array of ultrasound transducers in the joint positioner 100 advantageously allows for continuous registration of a portion of a patient's anatomy during a surgical procedure. In contrast, certain other methods of registration are typically performed prior to a surgical procedure or intermittently during a surgical procedure. These other methods may require the surgeon to perform steps such as using a probe to physically contact the patient's bone. Furthermore, interruptions in tracking of the patient can cause errors in registration, requiring the surgeon to stop the procedure in order to reregister the patient. Interruptions in tracking may be caused by an occlusion of a trackable marker or a sudden movement of a tracked object. In the surgical system 200 shown in FIG. 4, the array 54 of the joint positioner 100 can be utilized to continuously scan a portion of the patient's anatomy. Using information obtained by the array 54, the processing circuit can continuously register the portion of the patient's anatomy. This continuous registration prevents the surgeon from having to stop a surgical procedure to reregister the patient after an interruption of a global tracking system has caused a registration error.

The construction and arrangement of the systems and methods as shown in the various exemplary embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.). For example, some elements shown as integrally formed may be constructed from multiple parts or elements, the position of elements may be reversed or otherwise varied and the nature or number of discrete elements or positions may be altered or varied. Accordingly, all such modifications are intended to be included within the scope of the present disclosure. The order or sequence of any process or method steps may be varied or re-sequenced according to alternative embodiments. Also two or more steps may be performed concurrently or with partial concurrence. Such variation will depend on various factors, including software and hardware systems chosen and on designer choice. All such variations are within the scope of the disclosure. Likewise, software implementations could be accomplished with standard programming techniques with rule based logic and other logic to accomplish the various connection steps, processing steps, comparison steps and decision steps. Other substitutions, modifications, changes, and omissions may be made in the design, operating conditions and arrangement of the exemplary embodiments without departing from the scope of the present disclosure.

The present disclosure contemplates methods, systems and program products on any machine-readable media for accomplishing various operations. The embodiments of the present disclosure may be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage, other magnetic storage devices, solid state storage devices, or any other medium which can be used to carry or store desired program code in the form of machine-executable instructions or data structures and which can be accessed by a general purpose or special purpose computer or other machine with a processor. When information is transferred or provided over a network or another communications connection (either hardwired, wireless, or a combination of hardwired or wireless) to a machine, the machine properly views the connection as a machine-readable medium. Thus, any such connection is properly termed a machine-readable medium. Combinations of the above are also included within the scope of machine-readable media. Machine-executable instructions include, for example, instructions and data which cause a general purpose computer, special purpose computer, or special purpose processing machines to perform a certain function or group of functions.

What is claimed is:

1. A robot-aided knee arthroplasty system, comprising:
   a robotic device comprising a first holder for holding a first portion of a limb of a patient, a second holder for holding a second portion of the limb of the patient, and a plurality of backdriveable actuators operable to apply forces to the first holder and the second holder;
   a controller communicable with the robotic device and programmed to:
      control the robotic device to enable manual repositioning of the limb of the patient by counteracting weight of the limb by applying the forces to the first holder and the second holder such that the limb feels weightless to a user manually repositioning the first holder and the second holder;
      control the robotic device to apply an additional force configured to increase a gap distance at a joint between the first portion of the limb and the second portion of the limb; and
      collect measurements of the gap distance as the robotic device applies the force.

2. The system of claim 1, further comprising a tracking system configured to track markers affixed to the first portion and the second portion and to output tracking information, wherein the controller is programmed to collect the measurements of the gap distance based at least in part on the tracking information.

3. The system of claim 1, further comprising a surgical planning system configured to plan a position and orientation of a resection of a femur of the first portion for implantation of a femoral implant on the femur.

4. The system of claim 3, wherein the surgical planning system is configured to update the plan based on the measurements.

5. The system of claim 1, wherein the controller is programmed to determine a magnitude of the additional force.

6. The system of claim 1, wherein at least some of the backdriveable actuators are including in a jointed arm of the robotic device comprising a plurality of joints arranged in series.

7. The system of claim 1, wherein the controller is further programmed to control the robotic device to apply a torque configured to rotate the second portion relative to the first portion.

8. The system of claim 7, wherein the controller is programmed to determine a magnitude of the torque.

9. The system of claim 1, wherein the controller is further programmed to control the robotic device to rearrange the joint to different arrangements associated with different stages of a joint replacement surgery, at least one of the different arrangements facilitating the bone resection.

10. The robot-aided knee arthroplasty system of claim 1, wherein the controller is programmed to switch between in a first mode in which the controller causes the robotic device to hold the limb in a fixed position and a second mode in which the robotic device enable manual repositioning of the limb of the patient by a surgeon.

11. A method for robotically-assisted soft tissue balancing for an arthroplasty procedure, comprising:

controlling a robotic device to apply, using backdriveable actuators of the robotic device, forces to a first holder holding a first bone of a limb a second holder holding a second bone of the limb;

enabling manual repositioning of the limb of the patient by counteracting, by the forces, weight of the limb by applying the forces to the first holder and the second holder such that the limb feels weightless to a user manually repositioning the first holder and the second holder;

measuring a gap distance between the first bone and the second bone while an additional force is applied by the robotic device increasing the gap distance between the first bone and the second bone.

12. The method of claim 11, wherein the additional force has a known magnitude.

13. The method of claim 11, wherein measuring the gap distance is performed based at least in part on tracking data from a system configured to track relative positions of a first tracker attached to the first bone and a second tracker attached to the second bone.

14. The method of claim 11, comprising updating a surgical plan by determining a parameter of a bone resection based on the gap distance.

15. The method for claim 11, comprising selecting an implant based on the gap distance.

* * * * *